United States Patent
Hengstermann et al.

(10) Patent No.: US 8,362,299 B2
(45) Date of Patent: Jan. 29, 2013

(54) METHOD FOR PRODUCING AND PURIFYING AQUEOUS PHASES

(75) Inventors: Axel Hengstermann, Senden (DE);
Franz-Felix Kuppinger, Marl (DE);
Jorg Leistner, Rheda-Wiedenbruck (DE); Jurgen Mosler, Marl (DE); Peter Jansens, KV Sittard (NL)

(73) Assignee: Evonik Stockhausen GmbH, Krefeld (DE)

(*) Notice: Subject to any disclaimer, the term of this patent is extended or adjusted under 35 U.S.C. 154(b) by 133 days.

(21) Appl. No.: 12/921,527

(22) PCT Filed: Mar. 11, 2009

(86) PCT No.: PCT/EP2009/052831
§ 371 (c)(1),
(2), (4) Date: Nov. 8, 2010

(87) PCT Pub. No.: WO2009/130085
PCT Pub. Date: Oct. 29, 2009

(65) Prior Publication Data
US 2011/0046297 A1   Feb. 24, 2011

(30) Foreign Application Priority Data
Apr. 24, 2008 (DE) .......................... 10 2008 020 688

(51) Int. Cl.
C07C 51/42 (2006.01)
C07C 57/04 (2006.01)
(52) U.S. Cl. ........................................ 562/600; 422/618
(58) Field of Classification Search .................. 562/600; 422/618
See application file for complete search history.

(56) References Cited

U.S. PATENT DOCUMENTS

| | | | |
|---|---|---|---|
| 3,198,750 A | 8/1965 | Callahan et al. |
| 3,251,899 A | 5/1966 | Callahan et al. |
| 3,736,355 A | 5/1973 | Croci et al. |
| 3,865,873 A | 2/1975 | Oda et al. |

(Continued)

FOREIGN PATENT DOCUMENTS

| CA | 2282492 A1 | 9/1998 |
|---|---|---|
| CN | 1105352 | 7/1995 |

(Continued)

OTHER PUBLICATIONS

German language Written Opinion mailed on Aug. 31, 2009 in PCT/EP2009/052831.

(Continued)

*Primary Examiner* — Vu A Nguyen
(74) *Attorney, Agent, or Firm* — Smith Moore Leatherwood LLP; Philip P. McCann (57) ABSTRACT

The present invention relates to a method for purifying an unpurified phase, containing a target product, preferably (meth)acrylic acid, water, and at least one impurity differing from the target product and from water comprising: a) crystallizing the target product and water; b) separating the crystals from the mother liquor created in step a); c) melting at least part of the separated crystals to form a melt; and d) recycling at least part of said melt to step b). The invention further relates to a method for the production of a purified phase, containing a target product and water, a method for the production of a polymer based on (meth)acrylic acid, polymers that may be obtained by means of said method, chemical products, such as fibers or molded bodies, and the use of polymers.

16 Claims, 2 Drawing Sheets

U.S. PATENT DOCUMENTS

| | | | |
|---|---|---|---|
| 4,224,187 | A | 9/1980 | Vanderspurt |
| 4,267,386 | A | 5/1981 | Vanderspurt |
| 4,408,079 | A | 10/1983 | Merger et al. |
| 4,496,770 | A | 1/1985 | Duembgen et al. |
| 4,780,568 | A | 10/1988 | Pascoe |
| 5,463,121 | A | 10/1995 | Sridhar |
| 5,510,558 | A | 4/1996 | Umansky et al. |
| 5,705,684 | A | 1/1998 | Hefner et al. |
| 6,664,419 | B1 | 12/2003 | Bub et al. |
| 7,112,695 | B2 * | 9/2006 | Eck et al. .................. 562/600 |
| 7,141,707 | B2 | 11/2006 | Beckmann et al. |
| 7,294,741 | B2 | 11/2007 | Bub et al. |
| 7,557,245 | B2 | 7/2009 | Nordhoff et al. |
| 7,557,246 | B2 | 7/2009 | Nordhoff et al. |
| 2003/0175159 | A1 | 9/2003 | Heilek et al. |
| 2004/0116741 | A1 | 6/2004 | Nordhoff et al. |
| 2004/0256319 | A1 | 12/2004 | Hammon et al. |
| 2006/0013748 | A1 | 1/2006 | Nordhoff et al. |
| 2007/0203369 | A1 | 8/2007 | Praefke et al. |
| 2008/0251456 | A1 | 10/2008 | Wiese et al. |
| 2008/0287616 | A1 | 11/2008 | Balduf et al. |
| 2009/0023006 | A1 | 1/2009 | Bub et al. |
| 2009/0032465 | A1 | 2/2009 | Baumgarten et al. |
| 2009/0068440 | A1 | 3/2009 | Bub et al. |
| 2009/0134357 | A1 | 5/2009 | Bub et al. |
| 2009/0239995 | A1 | 9/2009 | Bub et al. |

FOREIGN PATENT DOCUMENTS

| | | |
|---|---|---|
| DE | 1205502 | 11/1965 |
| DE | 1962431 A1 | 6/1970 |
| DE | 2251364 A1 | 5/1973 |
| DE | 2943707 A1 | 5/1980 |
| DE | 4401405 A1 | 7/1995 |
| DE | 19508558 A1 | 9/1996 |
| DE | 10149353 A1 | 7/2002 |
| DE | 102005028624 A1 | 12/2006 |
| EP | 0058927 A1 | 9/1982 |
| EP | 0092097 A1 | 10/1983 |
| EP | 0117146 A1 | 8/1984 |
| EP | 0193226 A1 | 9/1986 |
| EP | 0253409 A2 | 1/1988 |
| EP | 0257565 A1 | 3/1988 |
| EP | 0293224 A1 | 11/1988 |
| GB | 1450986 | 9/1976 |
| JP | 57095938 | 6/1982 |
| WO | 9840342 A1 | 9/1998 |
| WO | 03078378 A1 | 9/2003 |
| WO | 2005118719 A2 | 12/2005 |
| WO | 2006022664 A2 | 3/2006 |

OTHER PUBLICATIONS

International Search Report mailed on Aug. 31, 2009 in PCT/EP2009/052831.

Kuppinger et al., U.S. Appl. No. 12/438,295, filed Feb. 20, 2009.

* cited by examiner

METHOD FOR PRODUCING AND PURIFYING AQUEOUS PHASES

This application is a national stage application under 35 U.S.C. 371 of International Application No. PCT/EP2009/052831 filed 11 Mar. 2009, which claims priority to German Application No. DE 10 2008 020 688.1 filed 24 Apr. 2008, the disclosures of which are expressly incorporated herein by reference.

The present invention relates to a process for the purification of an impure phase comprising a target product and water, to a process for the preparation of a purified phase comprising a target product and water, to a purified phase comprising a target product and water, to a process for the preparation of a polymer based on (meth)acrylic acid, to polymers obtainable by this process, to chemical products, such as, for example, fibers or moldings, and to the use of polymers.

BACKGROUND

In the production of industrially relevant target products, such as, for example, (meth)acrylic acid, aqueous compositions which also contain numerous impurities in addition to the desired target products and water are frequently obtained in the course of the production. Before (meth)acrylic acid can be used as starting material in the preparation of polymers by free radical polymerization, it was customary to date to isolate the (meth)acrylic acid from such aqueous compositions, a purity of more than 99% by weight frequently being strived for in the case of acrylic acid. In the preparation of poly(meth)acrylates from a high-purity (meth)acrylic acid obtained in this manner, the latter is then dissolved in water as a solvent and is polymerized in the presence of free radical initiators.

Crystallization may be mentioned as one possibility for the preparation of high-purity, organic substances, such as, for example, high-purity acrylic acid. In particular, two processes are used industrially, suspension crystallization and layer crystallization (Wintermantel et al., Chem. Ing. Tech. 1991, 63, 881-891; Steiner et al., Chem. Ing. Techn. 1985, 57, 91-102).

However, one crystallization step alone is often not enough for removing byproducts sufficiently well out of or from the crystals since microinclusions of mother liquors or the incorporation of impurities at crystal defects, etc. cannot be ruled out under finite crystal growth conditions. In particular, the adhesion of mother liquor to the crystal can adversely affect the purity of the products.

For this reason, the crystals produced are frequently, particularly in the case of a crystal suspension, washed with wash liquids after the separation from the mother liquor and/or, in the case of the layer or suspension crystallization, the crystals are subjected to a sweating or wash process in which impurities of any type can, if required, be depleted.

Such a process can be carried out continuously in a so-called wash column. An overview in this respect is given in the dissertation by Poschmann (Zur Suspensionskristallisation organischer Schmelzen und Nachbehandlung der Kristalle durch Schwitzen und Waschen [On the suspension crystallization of organic melts and aftertreatment of the crystals by sweating and washing], thesis, Uni. Bremen, Shaker Verlag, Aachen 1996).

Such a process in which (meth)acrylic acid crystals are crystallized out of an aqueous melt comprising (meth)acrylic acid, water and impurities differing from (meth)acrylic acid and water and the (meth)acrylic acid crystals thus obtained are at least partly washed with a crystal melt is described, for example, in WO-A-03/078378. According to the teaching of this publication, (meth)acrylic acid is crystallized from such an aqueous solution at a temperature in the range of −5 to 30° C., the crystals thus obtained are then melted at a temperature in the range from 10 to 15° C. and the (meth)acrylic acid crystals are then washed with the crystal melt.

However, the disadvantage of the process described in WO-A-03/078378 is, inter alia, that the crystal bed obtained there tends to a high degree of compaction so that it is necessary to use hydraulic pressure which is problematically high for industrial use, in particular with the use of continuously operated wash columns. Furthermore, the process described in WO-A-03/078378 has the disadvantage that a comparatively large amount of energy has to be applied for melting the (meth)acrylic acid.

SUMMARY

The present invention includes various embodiments as set forth herein.

In general, it is the object of the present invention to overcome the disadvantages arising out of the prior art by the provision of suitable technical teachings.

In particular, a process for the purification of an impure phase comprising a target product, in particular (meth)acrylic acid, and water is to be provided, which process can be carried out with apparatuses or apparatus components which are provided with as few technically complicated internals as possible in comparison with the apparatuses or apparatus components known from the prior art.

It was also the object of the present invention to provide a process for the purification of an impure phase comprising a target product, in particular (meth)acrylic acid, and water, which process can be operated as economically as possible from the energy point of view.

Moreover, this process for the purification of an impure phase comprising a target product, in particular (meth)acrylic acid, and water should be a crystallization process which can be carried out so efficiently that a further crystallization of the mother liquor obtained in the first crystallization is not required.

In addition, it was the object of the present invention to provide a process for the preparation of a polymer based on (meth)acrylic acid, which process can be operated as economically as possible. In particular, this process should make it possible to be able to dispense with a purification of (meth)acrylic acid to a purity of more than 90% by weight.

FIGURE

The forgoing and other features, aspects, and advantages of the present invention will become better understood with regard to the following description, appended claims, and accompanying drawing where:

DETAILED DESCRIPTION

These objects are achieved by a process for the purification of an impure phase comprising a target product, preferably (meth)acrylic acid, water and at least one impurity differing from the target product and from water to give a purified phase, having a process stage which comprises the following process steps:

a) the target product and water are crystallized out of the impure phase with formation of a suspension comprising a mother liquor and crystals, this crystallization being effected at a temperature $T_1$ in the range of $T_e-15°$ C.$\leq T_1 \leq T_e+3°$ C. ($T_e$=eutectic temperature of the impure phase), particularly preferably at a temperature $T_1$ in the range of $T_e-11°$ C.$\leq T_1 \leq T_e+2°$ C., even more preferably at a temperature $T_1$ in the range of $T_e-7°$ C.$\leq T_1 \leq T_e+1°$ C. and most preferably at a temperature $T_1$ in the range of $T_e-3°$ C.$\leq T_1 \leq T_e$;

b) the crystals are at least partly separated from the mother liquor;

c) at least a part of the crystals separated off is melted to give a melt, this melting being effected at a temperature $T_2$ in the range of $T_1 < T_2 \leq T_1+20°$ C., particularly preferably at a temperature in the range of $T_1 < T_2 \leq T_1+10°$ C., even more preferably at a temperature in the range of $T_1 < T_2 \leq T_1+5°$ C. and most preferably at a temperature in the range of $T_1 < T_2 \leq T_1+1°$ C.; and d) at least a part of the melt is recycled to step b), the non-recycled part of the melt being present as a purified phase.

If accordingly in the case of an acrylic acid-comprising, impure phase $T_e$ is, for example, $-11°$ C., the crystallization takes place in a range from $-26°$ C. to $-8°$ C., particularly preferably in a range from $-22°$ C. to $-9°$ C., even more preferably in a range from $-18°$ C. to $-10°$ C. and most preferably in a range from $-14°$ C. to $-11°$ C. If the crystallization takes place at $-11°$ C., the melting takes place at a temperature above $-11°$ C. up to $+9°$ C., particularly preferably at a temperature above $-11°$ C. up to $-1°$ C., even more preferably at a temperature above $-11°$ C. up to $-6°$ C. and most preferably at a temperature above $-11°$ C. up to $-10°$ C.

Surprisingly, it was found that compositions substantially based on water and a target product which additionally contain undesired impurities can be purified in a particularly simple and especially economical manner by cooling such compositions down to temperatures around the eutectic point and in this way forming water crystals and crystals of the target product. These crystals are separated from the remaining mother liquor and at least partly melted at that temperature which is only insignificantly higher than the crystallization temperature, the unmelted crystals being washed with a part of this melt. A part of the melt which is not used for washing represents a purified phase which comprises water and the target product and is depleted with respect to the impurities present therein in comparison with the originally used, impure phase.

This process is particularly advantageous in the case of target products which are present at some time in the course of their preparation from corresponding precursor compounds as an aqueous phase comprising the target product, and water and further impurities and which are used later likewise in the form of aqueous solutions in the further processing to give successor products. By means of the process according to the invention, it is in fact possible to dispense with the procedure in which the target products, for the purpose of separating off byproducts, are first produced in virtually completely purified form (and hence freed from water) and are then dissolved again in water in the further processing to give successor products, as is currently usual, for example, in the case of the preparation of acrylic acid and the subsequent preparation of polyacrylates from acrylic acid.

In this text, "(meth)acrylic acid" is used for the compounds with the nomenclature names "methacrylic acid" and "acrylic acid". Of the two compounds, acrylic acid is preferred according to the invention. According to the invention, the term "target product" is understood as meaning an organic compound which, in a two-component system comprising water and the organic compound, is capable of forming a eutectic mixture ("eutectic").

Although, in the case of (meth)acrylic acid as a target product, the impure phase is more greatly cooled in comparison to the process described in WO-A-03/078378, the quantity of energy to be applied for melting the crystals thus forming is smaller in the case of the process according to the invention which is now provided, since the crystals close to the eutectic point already melt at above $-11°$ C. Otherwise, in the case of the conventional procedure disclosed, for example, in WO-A-03/078378, it will be necessary to heat to temperatures of at least $0°$ C. again, which, as discussed at the outset, leads to problems in the case of a continuously operated wash column.

In step a) of the process stage present in the process according to the invention, the target product and water are first crystallized out of the impure phase with formation of a suspension comprising a mother liquor and crystals, in particular crystals of the target product and water crystals.

All compounds which are known to a person skilled in the art and are capable of forming a eutectic mixture in a two-component system with water and are present in the course of their industrial production from corresponding starting compounds at some time in the form of an aqueous phase comprising this target product, water and impurities differing from this target product and water are suitable as the target product.

According to the invention, unsaturated mono- or dicarboxylic acids are particularly preferred as the target product, among these acrylic acid and methacrylic acid being particularly preferred as the target product and acrylic acid being most preferred.

According to a first particular embodiment of the process according to the invention, the impure phase comprises, as a water-rich composition, acrylic acid in a concentration in a range from 40 to 75% by weight, particularly preferably 50 to 70% by weight and most preferably 55 to 65% by weight, water in a concentration in a range from 20 to 55% by weight, particularly preferably 28 to 48% by weight and most preferably 34 to 44% by weight, and impurities differing from water and acrylic acid in a concentration of not more than 15% by weight, particularly preferably not more than 10% by weight, even more preferably not more than 5% by weight and most preferably not more than 1% by weight, based in each case on the composition. Such an impure phase may originate, for example, from a quench absorber. Furthermore, the impure phase may be a mother liquor depleted in acrylic acid or the filtrate from a crystallization whose acrylic acid is furthermore to be purified. Such an impure phase may also be obtained by the deliberate addition of one of the components present in the impure phase, for example by the deliberate addition of water, to a phase in which the individual components are not present in the abovementioned concentration ranges, so that, deliberate addition of these components results in an impure phase which contains acrylic acid, water and impurities differing from acrylic acid and water in the abovementioned concentration ranges. According to a particular variant of this first preferred embodiment of the process according to the invention, the impure phase used in process step a) comprises 58 to 62% by weight of acrylic acid, 37 to 41% by weight of water and 1 to 2% by weight, based in each case on the impure phase, of acrylic acid and impurities differing from water.

According to a second particular embodiment of the process according to the invention, the impure phase comprises, as a water-rich composition, methacrylic acid in a concentration in a range from 2 to 40% by weight, particularly preferably 5 to 25% by weight, even more preferably 8 to 20% by weight and most preferably 10 to 15% by weight, water in a concentration in a range from 60 to 98% by weight, particularly preferably 75 to 95% by weight, even more preferably 80 to 92% by weight and most preferably 85 to 90% by weight, and the purities differing from water and methacrylic acid in a concentration of not more than 10% by weight, particularly preferably not more than 5% by weight, even more preferably not more than 1% by weight and most preferably not more than 0.1% by weight, based in each case on the composition. According to a particular variant of this second preferred embodiment of the process according to the invention, the impure phase used in process step a) comprises 9 to 14% by weight of methacrylic acid, 85 to 90% by weight of water and 1 to 2% by weight, based in each case on the impure phase, of impurities differing from methacrylic acid and water. Such an impure phase is obtained, for example, as a discharge in the quench absorber in the preparation of methacrylic acid.

In the crystallization, the crystallization means to be used are preferably those which make it possible to design the purification process according to the invention as a continuous process. Suspension crystallization is preferably used. This can advantageously be carried out in a stirred tank crystallizer, scraped surface crystallizer, cooling disc crystallizer, crystallizing coil, drum crystallizer, tube-bundle crystallizer or the like. In particular, the crystallization variants mentioned in WO-A-99/14181 can be used for the said purpose. Once again, those crystallizers which can be operated continuously are particularly advantageous here. These are preferably the cooling disc crystallizers or the scraped surface coolers (thesis by Poschmann, page 14). A scraped surface cooler is very particularly preferably used for the crystallization.

Furthermore, it is preferable according to the invention if the crystallization in process step a) is effected at a temperature $T_1$ in the range of $T_e-15° C. \leq T_1 \leq T_e+3° C.$ ($T_e$=eutectic temperature of the impure phase), particularly preferably at a temperature $T_1$ in the range of $T_e-11° C. \leq T_1 \leq T_e+2° C.$, even more preferably at a temperature $T_1$ in the range of $T_e-7° C. \leq T_1 \leq T_e+1° C.$ and most preferably at a temperature $T_1$ in the range of $T_e-3° C. \leq T_1 \leq T_e$.

According to the first particular embodiment of the process stage present in the process according to the invention, in the case of acrylic acid as the target product, the crystallization in process step a) is effected at a temperature $T_1$ in a range from −8° C. to −26° C., even more preferably in a range from −9° C. to −22° C., even more preferably in a range from −10° C. to −18° C. and most preferably in a range from −11° C. to −14° C. According to the second particular embodiment of the process stage present in the process according to the invention, in the case of methacrylic acid as the target product, the crystallization in process step a) is effected at a temperature $T_1$ in a range from +6° C. to −26° C., even more preferably in a range from +2° C. to −16° C. and most preferably in a range from 0° C. to −10° C.

In step b) of the process stage present in the process according to the invention, the crystals which are obtained in process step a) and are present as a mixture of crystals of the target product and water crystals are separated from the mother liquor, it being advantageous here too to use, for separating the crystals from the mother liquor, an apparatus by means of which the separation can be carried out continuously. In the case of layer crystallization or static crystallization, the separation of the crystals from the mother liquor can be effected in the crystallization apparatus itself since the crystals are fixed to the apparatus and the mother liquor can be removed by allowing it to flow out of the apparatus. The removal of the crystals from the crystallization apparatus is effected by melting the crystals and subsequently allowing the melt to flow away. In the case of suspension crystallization, all known solid-liquid separation methods are suitable. In a particular embodiment of the invention, the crystals are separated from the mother liquor by filtration and/or centrifuging. Advantageously, a preliminary thickening of the suspension, for example by hydrocyclone(s), is included upstream of the filtration or centrifuging. All known centrifuges which operate batchwise or continuously are suitable for the centrifuging. Pusher centrifuges which can operate in one or more stages are most advantageously used. In addition, spiral screen centrifuges or helical-conveyor centrifuges (decanters) are also suitable. Filtration is advantageously effected by means of suction filters which are operated batchwise or continuously, with or without a stirrer, or by means of belt filters. In general, the filtration can be effected under pressure or in vacuo.

Particularly preferred according to the invention is the use of a wash column in which the separation of the mother liquor according to process step b) and the washing with the at least partly molten crystals according to process step d) are effected in one apparatus. Such a wash column advantageously has a separating region in which the crystals of the target product and the water crystals are washed. For the successful operation of a wash column, it is advantageous for the crystals to be washed to be sufficiently hard and to have a certain narrow size distribution in order to ensure sufficient porosity, permeability and stability and as low a compressibility as possible of the resulting packed or non-packed filter bed.

In principle, any wash column which permits continuous operation of the purification according to the invention or quasi-continuous operation, as is effected, for example, in the wash columns with mechanical bed transport from Niro Process Technology B.V., in s'Hertogenbusch (The Netherlands), can be used for the process according to the invention. In a customary embodiment, the suspension is added to a hydraulic wash column in any desired region of the column, for example in the upper part of the column; the mother liquor is taken off from the column via a filter, with the result that a tightly packed crystal bed forms. The mother liquor and recycled mother liquor flows through the crystal bed already formed above the filter unit in the direction of that side of the column which is opposite the feed and said crystal bed is forced in this direction by the flow resistance. Such a wash column and the mode of operation thereof are described, for example, in WO-A-2004/026429, the disclosure content of which with regard to the design and the mode of operation of the wash column is herewith incorporated by reference and forms a part of the disclosure of the present application.

In the case of a mechanical wash column—reference may be made by way of example also to EP-A-0 193 226 B—a dense crystal bed is produced within the column by means of a piston permeable to the melt. The piston may be present at the upper or lower end of the column; the feeding of the suspension takes place in the upper region of the column in the first case and in the middle or lower region in the second case. The piston is permeable to the melt so that, on compression, melt emerges at the back of the piston and is taken off there.

Embodiments for suspension crystallization with downstream washing of the crystals in a hydraulic or mechanical wash column are described in the book *Melt Crystallization Technology* by G. F. Arkenbout, Technomic Publishing Co.

Inc., Lancaster-Basel (1995), pages 265-288, and the article in Chemie Ingenieur Technik (72) (October 2000), 1231-1233, which relates to the Niro freeze concentration for wastewater preconcentration.

In step c) of the process stage present in the process according to the invention, at least part of the crystals separated off are melted to give a melt. This can be affected by melting a part of the crystals after separation from the mother liquor or, which is preferred according to the invention, resuspending a part of the crystals and melting the crystals in the suspension thus obtained.

Where a wash column is used, the melting in process step c) is particularly preferably effected in such a way that a moving, preferably rotating scraped surface apparatus or a rotating scraper which is mounted on that side of the column which is opposite the feed produces a suspension again from crystals of the tightly packed crystal bed and the wash melt introduced according to process step d). This suspension is preferably pumped through a melter, preferably a heat exchanger, and melted. A part of the melt can serve, for example, as wash melt; this is then pumped back into the column and preferably washes the crystal bed migrating in the opposite direction, i.e. the crystallized target product and the crystallized water are washed countercurrently by the recycled melt comprising water and the target product. Firstly, the wash melt washes the crystals and secondly the melt crystallizes at least partly on the crystals. The enthalpy crystallization liberated heats the crystal bed in the wash region of the column. Firstly, purification is effected thereby by the washing of the surface of the water crystals and the target product crystals with melted water and molten target product (i.e. with a molten phase comprising water and target product) and secondly healing or sweating-out of impurities is achieved by the crystallization of the molten phase comprising target product and water on the crystals of the target product which are already present and on the water crystals already present. This permits the preparation of a high-purity, aqueous phase of the target product, i.e. an aqueous phase which comprises virtually exclusively water and target product).

In relation to process step c), it is in particular preferable if the melting is effected at a temperature in the range of $T_1 < T_2 \leq T_2 + 20°$ C., particularly preferably at a temperature in the range of $T_1 < T_2 \leq T_2 + 10°$ C., even more preferably at a temperature in the range of $T_1 < T_2 \leq T_2 + 5°$ C. and most preferably at a temperature in the range of $T_1 < T_2 \leq T_2 + 1°$ C. It is particularly preferable if the melting in process step c) is effected at a temperature $T_2$ which is 0.1 to 15 degrees, particularly preferably 0.5 to 10 degrees, even more preferably 1 to 5 degrees and most preferably 2 to 4 degrees above the temperature $T_1$.

In the case of acrylic acid as target product, according to the first particular embodiment of the process stage present in the process according to the invention, the melting in process step c) is effected at a temperature $T_2$ in a range above $-11°$ C. to 9° C., particularly preferably in a range above $-11°$ C. to $-1°$ C., even more preferably in a range above $-11°$ C. to $-6°$ C. and most preferably in a range above $-11°$ C. to $-10°$ C. In the case of methacrylic acid as target product, according to the second particular embodiment of the process stage present in the process according to the invention, the crystallization in process step a) is effected at a temperature $T_1$ in a range from $+7°$ C. to $-25°$ C., even more preferably in a range from $+3°$ C. to $-15°$ C. and most preferably in a range from $1°$ C. to $-9°$ C.

In step d) of the process stage present in the process according to the invention, a part of the melt is recycled to step b), this recycling being effected in particular by the procedure described above, in which a suspension is produced again in the lower part of the wash column from the crystals of the crystal bed and the wash melt obtained in process step c), this suspension is then pumped through a melter, preferably a heat exchanger, and melted and a part of the melt then serves as wash melt, which is pumped back into the column and washes the crystal bed migrating in the opposite direction.

In a special configuration of the process according to the invention, the recycle stream which results from the recycling of the molten crystals from step c) in step b) is greater than a feed stream of the impure phase which is fed continuously from outside to step a). In particular, the recycle stream is at least just as large, preferably at least twice as large, even more preferably at least four times as large and most preferably at least ten times as large as the feed stream. The large recycle stream ensures that thermal loading of the target product at the melter is reduced.

For seeding of the target product to be crystallized, it may prove to be advantageous to feed the isolated, crystallized target product b) at least partly into step a). The recycled target product crystals facilitate the crystal growth in step a) and thus promote the separation of the target product from the mother liquor. This is advantageous particularly in the case of a highly aqueous composition.

On the basis of energy considerations, a one-stage purification process with only one process stage is in principle particularly advantageous and therefore particularly preferred. Under certain circumstances, however, a two-stage purification process is expedient. Regarding the carrying out of a two-stage or multistage purification process, reference is made in particular to WO-A-03/078378, the disclosure content of which with regard to a purification process comprising two process stages with process steps a) to d) is hereby incorporated by reference and forms part of the disclosure of the present invention.

In a particular configuration of the process according to the invention, the purified phase is purified in a further purification process, in particular purification processes in which the water present in the purified phase can optionally be separated partly from the target product. Suitable purification processes are sufficiently well known to a person skilled in the art. Specifically, the following such processes are preferably used:

1. Simple Distillation

The purification of a composition mainly comprising water and target product for the purpose of separating off the water is carried out in a majority of cases by means of azeotropic rectification. For example, entraining agents such as toluene or MIBK are used (cf. EP 0 695 736 B1).

2. Extraction of the Target Product

The target product can be obtained by extraction using suitable extracting agents. The extraction of organic compounds from aqueous compositions is part of the prior art. Target products such as acrylic acid and methacrylic acid can be extracted, for example, with liquid ion exchangers, mixtures of tri-n-alkylamines and aliphatic alcohols or n-butanol (Vogel et al.: Chem. Eng. Technol. 23 (2000)1, pages 70-74; Tamada et al. in "*Solvent Extraction*", 1990, editor: T. Sekine, Elsevier Science Publishers B.V., pages 1791-1796; JP 57 095 938; WO-A-98/40342; information brochure of Sulzer Chemtech on the fractional extraction of (meth)acrylic acid with n-butanol).

3. Dewatering of the Target Product by Pervaporation

This process is disclosed, inter alia, in DE 44 01 405 A1.

4. Dewatering of the Target Product by Crystallization

Furthermore, the purified phase obtainable by the process according to the invention and comprising water and the target product can also be freed from at least a part of the water by further crystallization steps, in particular by crystallization steps according to the process according to the invention.

However, it should be emphasized once again at this point that, in particular in the case of target products which are used subsequently in the further processing to give successor products likewise in the form of aqueous solutions, further purification steps, in particular separating off water, are usually dispensible. Simply by means of the crystallization process according to the invention, impurities can be depleted to such a great extent that the aqueous phase obtainable by the process according to the invention can be used directly for the preparation of successor products.

A contribution to the achievement of the objects mentioned at the outset is also made by a process for the preparation of a purified phase comprising a target product, preferably (meth) acrylic acid, and water, comprising the process steps:

($\alpha$1) provision of an impure, aqueous phase comprising the target product, water and impurities differing from the target product and from water;

($\alpha$2) purification of the impure, aqueous phase by the process described above for the purification of an impure phase comprising the target product, water and at least one impurity differing from the target product and water.

In process step ($\alpha$1), an impure, aqueous phase comprising the target product, water and impurities differing from the target product and from water is first prepared. In principle, all processes known to the person skilled in the art which, depending on the target product, lead in the end to the provision of such an impure, aqueous phase, are suitable here. Usually, this aqueous phase is any aqueous phase which is obtained as a reaction mixture in the course of industrial production of the target product from a corresponding starting compound. In particular, suitable aqueous phases here are those which are obtained if the starting compound is reacted in water as solvent or aqueous phases which are obtained if a starting substance is reacted in the gas phase and the gaseous reaction mixture thus obtained, which contains the target product, is absorbed in water.

In the case of acrylic acid as target product, for example, a process in which first 3-hydroxypropionic acid is prepared from suitable precursor compounds by a fermentation route and this 3-hydroxypropionic acid is then dehydrated with formation of crude (meth)acrylic acid is conceivable as process step ($\alpha$1). Such a process is described, for example, in WO-A-2006/022664 or in WO-A-2005/118719. A process in which first glycerol is dehydrated with formation of acrolein and the acrolein thus obtained is converted into acrylic acid, as described, for example, in DE-A-10 2005 028 624, is furthermore conceivable.

According to a preferred embodiment of the process according to the invention for the preparation of a purified phase comprising a target product and water, in which the target product is (meth)acrylic acid, however, process step ($\alpha$1) comprises the following process steps:

($\beta$1) preparation of a product mixture containing (meth) acrylic acid by catalytic gas-phase oxidation of suitable $C_3$ or $C_4$ compounds;

($\beta$2) absorption of the product mixture containing (meth) acrylic acid in water to give a first, aqueous phase;

($\beta$3) optionally at least partial separation of water from the first, aqueous phase to give a second, aqueous phase.

In process step ($\beta$1), a product mixture containing (meth) acrylic acid is first prepared by catalytic gas-phase oxidation of suitable $C_3$ or $C_4$ compounds.

According to the invention, acrylic acid or methacrylic acid is preferably prepared in process step ($\beta$1) by catalytic gas-phase oxidation of $C_3$- or $C_4$-alkanes, -alkenes, -alkanols and/or -alkanals and/or precursors thereof. Particularly advantageously, acrylic acid or methacrylic acid is prepared by catalytic gas-phase oxidation of propene, acrolein, tert-butanol, isobutene, isobutane, isobutyraldehyde, methacrolein, isobutyric acid or methyl tert-butyl ether. All precursors of the said compounds in which the actual $C_3/C_4$ starting compound is first formed as an intermediate during the gas-phase oxidation can be used as starting compounds. Methyl tert-butyl ether or isobutyric acid may be mentioned by way of example for the preparation of methacrylic acid.

Particularly advantageous is the catalytic gas-phase reaction of propene and/or acrolein with molecular oxygen by known processes to give acrylic acid, in particular as described in the publications DE-A-19 62 431, DE-A-29 43 707, DE-PS 12 05 502, EP-A-0 257 565, EP-A-0 253 409, DE-AS 22 51 364, EP-A-0 117 146, GB-PS 1 450 986 and EP-A-0 293 224. Temperatures between 200 and 450° C. and optionally elevated pressure are preferably employed here. Preferably used heterogeneous catalysts are oxidic multicomponent catalysts based on the oxides of molybdenum, bismuth and iron in the first stage (oxidation of propene to acrolein) and the oxides of molybdenum and vanadium in the second stage (oxidation of acrolein to acrylic acid). If propane is used as a starting material, this can be converted into a propene/propane mixture by: catalytic oxydehydrogenation, as described, for example, in Catalysis Today 24 (1995), 307-313 or U.S. Pat. No. 5,510,558; by homogeneous oxydehydrogenation, as described, for example, in CN-A-1 105 352; or by catalytic dehydrogenation, as described, for example, in EP-A-0 253 409, EP-A-0 293 224, DE-A-195 08 558 or EP-A-0 117 146. With the use of a propene/propane mixture, propane acts as a diluent gas. Suitable propene/propane mixtures are also refinery propene (70% propene and 30% propane) or cracker propene (95% propene and 5% propane). In principle, propene/propane mixtures such as the abovementioned ones can be oxidized with oxygen or air or a mixture of oxygen and nitrogen of any composition to give acrolein and acrylic acid.

In the catalytic gas-phase oxidation, it is not pure acrylic acid which is obtained but a gaseous mixture which, in addition to the acrylic acid, may contain, as secondary components, substantially unconverted acrolein and/or propene, steam, carbon monoxide, carbon dioxide, nitrogen, propane, oxygen, acetic acid, propionic acid, formaldehyde, further aldehydes and maleic anhydride. Usually, the reaction product mixture contains, based in each case on the total reaction mixture, 1 to 30% by weight of acrylic acid, 0.05 to 1% by weight of propene and 0.05 to 1% by weight of acrolein, 0.05 to 10% by weight of oxygen, 0.05 to 2% by weight of acetic acid, 0.01 to 2% by weight of propionic acid, 0.05 to 1% by weight of formaldehyde, 0.05 to 2% by weight of aldehydes, 0.01 to 0.5% by weight of maleic anhydride and 20 to 98% by weight, preferably 50 to 98% by weight, of inert diluent gases. Inert diluent gases present are in particular saturated C1-C6-hydrocarbons, such as 0 to 90% by weight of methane and/or propane, and additionally 1 to 30% by weight of steam, 0.05 to 15% by weight of carbon oxides and 0 to 90% by weight of nitrogen, based in each case on 100% by weight of diluent gas.

Methacrylic acid can be prepared analogously to acrylic acid by catalytic gas-phase reaction of $C_4$ starting compounds with molecular oxygen. Particularly advantageously, methacrylic acid is obtainable, for example, by catalytic gas-phase oxidation of isobutene, isobutane, tert-butanol, isobutyraldehyde, methacrolein or methyl tert-butyl ether. Catalysts used are likewise transition metal mixed oxide catalysts (e.g. Mo, V, W and/or Fe). Particularly suitable processes are those in which the preparation is effected starting from methacrolein, in particular when the methacrolein is produced by gas-phase catalytic oxidation of tert-butanol, isobutane or isobutene or by reaction of formaldehyde with propionaldehyde according to EP-B-0 092 097 or EP-B-0 058 927. Thus, it is also possible to prepare methacrylic acid in two stages by (1) condensation of propionaldehyde with formaldehyde (in the presence of a secondary amine as a catalyst) to give methacrylic acid and (2) subsequent oxidation of the methacrolein to methacrylic acid.

As in the preparation of acrylic acid, it is not pure methacrylic acid which is obtained but a gaseous mixture which, in addition to methacrylic acid, may contain, as secondary components, substantially unconverted methacrolein and/or steam, carbon monoxide, carbon dioxide, nitrogen, oxygen, acetic acid, propionic acid, further aldehydes and maleic anhydride. The process according to the invention is used in particular when the reaction mixture contains 0.02 to 2% by weight of methacrolein, based on the total reaction mixture, and otherwise substantially the same corresponding constituents as in the case of the preparation of acrylic acid.

In process step ($\beta$2), the product mixture obtained in process step ($\beta$1) and containing (meth)acrylic acid is absorbed in water to give a first, aqueous phase, this absorption preferably being effected in suitable quench apparatuses. Advantageously, the condensation is carried out using a direct condenser, condensate already produced being brought into contact with the hot gaseous reaction product. Suitable apparatuses for the condensation are in particular spray scrubbers, Venturi scrubbers, bubble columns or apparatuses with sprayed surfaces.

In process step ($\beta$3), the first aqueous phase obtained in process step ($\beta$2) can optionally be further purified, in particular separating off the water by azeotropic distillation with suitable separating agents, such as, for example, toluene, being suitable here. After at least a part of the water has been separated off, a second aqueous phase is obtained.

In process step ($\alpha$2), the first aqueous phase or the second aqueous phase is then used as "impure phase" in the process according to the invention for the purification of an impure phase comprising a target product, preferably (meth)acrylic acid, water and at least one impurity differing from the target product and water.

A purified phase comprising a target product, preferably (meth)acrylic acid, and water, obtainable by the process described above, also makes a contribution to achieving the object mentioned at the outset.

A process for the preparation of a polymer based on (meth) acrylic acid also makes a contribution to achieving the objects mentioned at the outset, a purified phase comprising (meth) acrylic acid and water, prepared by the process described above for the preparation of a purified phase comprising (meth)acrylic acid as target product and water, or a purified phase obtainable by the process described at the outset for the purification of an impure phase comprising (meth)acrylic acid as target product, water and at least one impurity differing from (meth)acrylic acid and water being polymerized. Polymerization is preferably effected as solution polymerization, the reaction particularly preferably being carried out in a trough belt. Here, either the purified phase comprising (meth)acrylic acid as target product and water is used immediately or optionally is diluted appropriately beforehand. In general, the polymerization is effected in a medium, in the case of acrylic acid at a solids content (solid means all components of the monomer solution which differ from water and dissolved gases) in a range from 20 to 50% by weight, particularly preferably in a range from 30 to 40% by weight.

According to a preferred embodiment of this process according to the invention for the preparation of a polymer based on (meth)acrylic acid, the purified phase used in the polymerization is not further purified before the polymerization. In particular, preferably less than 20% by weight, particularly preferably less than 10% by weight, even more preferably less than 5% by weight, of water and most preferably no water at all is separated from this phase before the polymerization is carried out.

A contribution to achieving the objects mentioned at the outset is also made by a polymer obtainable by the process described above. The polymer is preferably an absorbing polymer having a maximum uptake of 0.9% strength by weight aqueous NaCl solution according to ERT 440.2-02 in a range from 10 to 1000, preferably from 15 to 500 and particularly preferably from 20 to 300 ml/g. Further details on absorbing polymers and the preparation thereof appear in "*Modern Superabsorbent Polymer Technology*", Fredric L. Buchholz, Andrew T. Graham, Whiley-VCH, 1998.

A contribution to achieving the object mentioned at the outset is also made by fibers, moldings, films, foams, superabsorbent polymers, special polymers for the areas of wastewater treatment, emulsion paints, cosmetics, textiles, leather finishing or papermaking or hygiene articles, at least based on or comprising a polymer obtainable by the process according to the invention for the preparation of a polymer.

A further contribution to achieving the objects mentioned at the outset is made by the use of a polymer obtainable by the process according to the invention for the preparation of a polymer, for the production of fibers, moldings, films, foams, superabsorbent polymers or hygiene articles, detergents or special polymers for the areas of wastewater treatment, emulsion paints, cosmetics, textiles, leather finishing or papermaking.

Further details and advantageous further developments of the present invention are explained in more detail with reference to the following drawing, which is intended to illustrate the invention by way of example, and with reference to an example.

Figure 1:
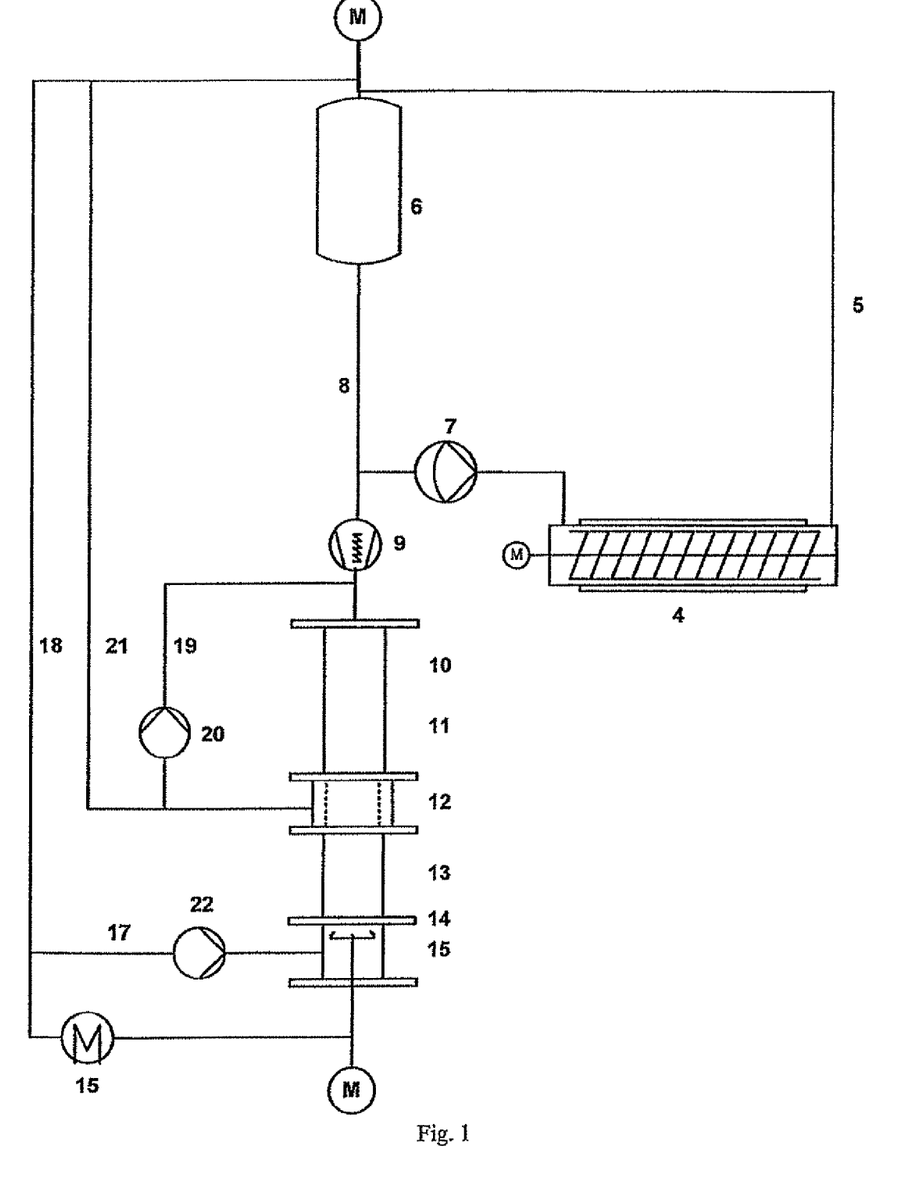
FIG. 1 is a graph showing the odor-binding effect of zinc salicylate in a superabsorber.

FIG. 1 schematically shows an experimental plant for carrying out the purification process according to the invention.

Figure 2:
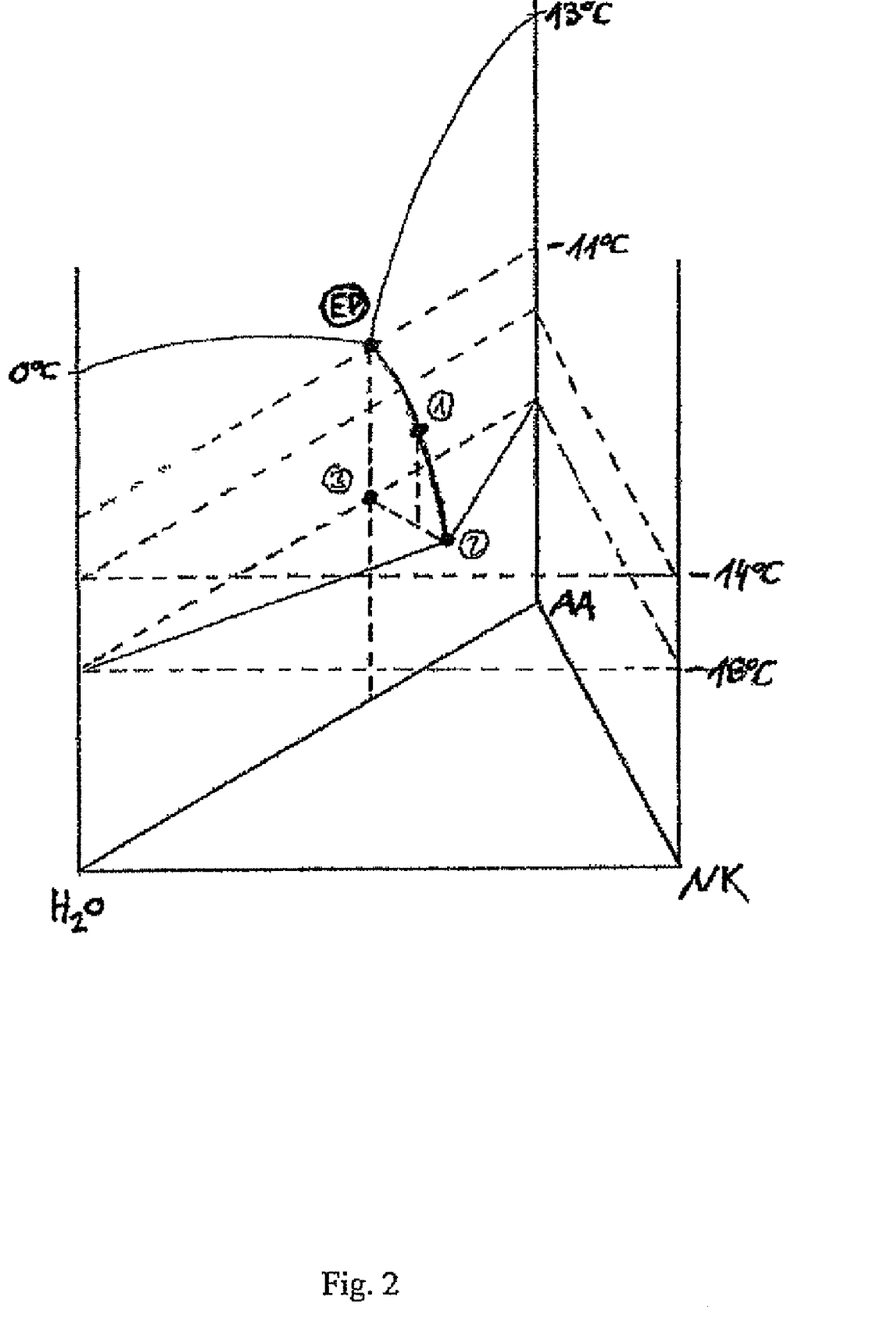

FIG. 2 shows the phase diagram for the pseudo-ternary composition used in Example 1.

EXAMPLE

A pseudo-ternary mixture of 59.4% by weight of acrylic acid, 39.4% by weight of water and 1.2% by weight of impurities differing from acrylic acid and water is purified according to the process according to the invention, the experimental arrangement shown in FIG. 1 having been used.

The hydraulic wash column used had an outer jacket filter (12) corresponding to a Philipps wash column known to a person skilled in the art and had a mechanically rotating crystal take-up (14) corresponding to a TNO wash column known to the person skilled in the art. The wash column installed had an internal diameter of 82 mm, a feed region (10) and sedimentation region (11) of 500 mm altogether and a wash region (13) of 300 mm length. The feed is supplied via a positively conveying screw pump (9). With the aid of a filtrate circulation pump (20), the filtrate was recycled to the feed region (10) of the wash column. The necessary force for transporting the crystal bed was applied by means of the differential pressure building up during flow through the crystal bed formed before the filtration unit (12). The maximum filtrate circulation flow (19) of the filtrate circulation pump (20) was 2.5 m³/h. The melting region (15) was equipped with a heat exchanger (16) having an exchange area of 1 m² and a circulation pump (17) having a maximum delivery of 1 m³/h for recycling the product melt (17) into the melting region (15).

An aqueous acrylic acid mixture comprising acrylic acid, water and secondary components corresponding to the composition from Table 1 was cooled down to a temperature of −14° C. with the aid of a scraped surface crystallizer (4) from Armstrong. The first crystals were observed on falling below −14° C.; this corresponds to point 1 in the pseudo-ternary phase diagram which is shown schematically in FIG. 2. By a further temperature reduction to −18° C., it was possible to produce a suspension (5) having a solids content of about 33% by weight. For ripening the crystals, the suspension was recycled into a dwell tank (5) with the aid of a circulation pump (7). According to the phase diagram, mother liquor (2) and crystal phase (3) were present in equilibrium at this temperature. The composition of the respective phases can likewise be seen in Table 1.

The suspension (8) produced is introduced via the positively conveying screw pump (9) from the dwell tank (6) into a first region (10), the feed region of the hydraulic wash column, a cylindrically shaped cavity. In the second zone (11), the binary crystal phase settles to give a compact crystal bed with recycling of the mother liquor by means of a control pump. The crystal bed consisting of water crystals, acrylic acid crystals and impure mother liquor was transported into the next region (12) in which the mother liquor was separated off via the filter installed in the outer jacket. The binary crystal phase was transported further through the cylindrical cavity and fed to the wash region (13). Here, washing of the crystals of the binary crystal phase with back-flowing, molten product was effected countercurrently. The washed binary crystal phase was removed from the crystal bed via the rotating knife (14) and fed to the melting region (15). Total melting of the remaining crystals at a temperature of −14° C. was effected in the downstream heat exchanger (16). A part of the molten product (17) was recycled via the melt circulation pump (22) into the wash region (13) as wash liquid. The temperature jump required for regulating the wash front was brought about by the equilibrium temperature at the crystallization point in the pseudo-ternary mixture of the feed region (10) and the melting point of the binary crystal phase consisting of water and acrylic acid, the eutectic temperature, in the melting region (15) (cf. FIG. 2).

At a feed rate (8) of 40 kg/h and a suspension density of 33%, an average product quantity (18) of 13.3 kg/h of a water/acrylic acid mixture could be removed. A stream of 26.7 kg/h was measured as mother liquor (21) and recycled into the dwell tank (6). For transporting the crystal bed through the cylindrical cavity, a control stream (19) of 600 kg/h was necessary. The control stream (19) was produced via the installed control stream pump (21). A maximum internal pressure in the feed region (10) of 4 bar resulted thereby. A pressure drop of about 3 bar was measured over the sedimentation zone (11). A wash pressure of 300 mbar was measured over the wash region (13). The temperature jump within the crystal bed in the wash region (10), the so-called wash front, was set at a height of 150 mm above the rotating knife (14) by regulating the product quantity.

Corresponding samples were taken of feed (1), mother liquor (2) and product (3) and analyzed by means of GC analysis or Karl Fischer titration. The results are shown in Table 1.

TABLE 1

| Analyses | | | |
|---|---|---|---|
| | Feed (1) | Mother liquor (2) | Product (3) |
| Acrylic acid | 59.4% | 58.2% | 61.8% |
| Water | 39.4% | 40.0% | 38.1% |
| Secondary components | 1.2% | 1.8% | 0.1% |

The product thus obtained and comprising water and acrylic acid can be used immediately for the preparation of polyacrylates.

The invention claimed is:

1. A process for the purification of an impure phase comprising a target product, water and at least one impurity differing from the target product and from water, comprising:
   a) crystallizing said target product and said water out of said impure phase to form a suspension comprising a mother liquor and crystals, wherein said crystallization is effected at a temperature $T_1$ in the range of $T_e - 15°$ C. $\leq T_1 \leq T_e + 3°$ C.;
   b) separating at least part of said crystals from said mother liquor;
   c) melting said at least a part of said crystals forming a melt, wherein said melt is effected at a temperature $T_2$ in the range of $T_1 < T_2 \leq T_1 + 10°$ C.; and
   d) recycling at least a part of said melt to step b), wherein said non-recycled part of the melt is purified.

2. The process according to claim 1, wherein said target product comprises (meth)acrylic acid.

3. The process according to claim 2, wherein said crystallizing of process step a) comprises being effected at a temperature $T_1$ in a range from −8° C. to −26° C. in the case of acrylic acid as said target product and at a temperature $T_1$ in a range from +2° C. to −26° C. in the case of methacrylic acid as said target product.

4. The process according to claim 2, wherein said crystallizing of process step a) comprises being effected at a temperature $T_1$ in a range from −9° C. to −22° C. in the case of acrylic acid as said target product and at a temperature $T_1$ in a range from 2° C. to −16° C. in the case of methacrylic acid as said target product.

5. The process according to claim 2, wherein said crystallizing of process step a) comprises being effected at a temperature $T_1$ in a range from −10° C. to −18° C. in the case of acrylic acid as said target product and at a temperature $T_1$ in a range from 0° C. to −10° C. in the case of methacrylic acid as said target product.

6. The process according to claim 1, wherein said melting of process step c) comprises being effected at a temperature $T_2$; wherein $T_2$ is from 0.1 to 10 degrees above said temperature $T_1$.

7. The process according to claim 1, said impure phase having a content of not more than 10% by weight, based on the impure phase, of compounds differing from said target product and said water.

8. The process according to claim 1, said crystals being washed countercurrently by said melt recycled into process step b).

9. The process according to claim 1, further comprising purifying said purified melt in a further purification process.

10. The process according to claim 1, further comprising recycling said mother liquor separated in step b) to step a).

11. The process according to claim 2, further comprising providing said impure phase by:
- (β1) preparing a product mixture comprising (meth)acrylic acid by catalytic gas-phase oxidation of suitable $C_3$ or $C_4$ compounds;
- (β2) absorbing said product mixture in water to give a first, aqueous phase;
- (β3) optionally at least partially separating water from the first, aqueous phase to give a second, aqueous phase, wherein said impure phase comprises said first, aqueous phase or said second, aqueous phase.

12. The process according to claim 1, wherein said crystallization of process step a) is effected at a temperature $T_1$ in the range of $T_e - 7°C. \leq T_1 \leq T_e + 1°C$.

13. The process according to claim 1, wherein said crystallization of process step a) is effected at a temperature $T_1$ in the range of $T_e - 3°C. \leq T_1 \leq T_e$.

14. The process according to claim 1, wherein said melt of process step c) is effected at a temperature $T_2$ in the range of $T_1 < T_2 \leq T_1 + 5°C$.

15. The process according to claim 1, wherein said melt of process step c) is effected at a temperature $T_2$ in the range of $T_1 < T_2 \leq T_1 + 1°C$.

16. The process according to claim 1, wherein said crystallization of process step a) is effected at a temperature $T_1$ in the range of $T_e - 3°C. \leq T_1 \leq T_e$ and said melt of process step c) is effected at a temperature $T_2$ in the range of $T_1 < T_2 \leq T_1 + 1°C$.

* * * * *